United States Patent [19]

Fåhraeus et al.

[11] Patent Number: 6,014,210
[45] Date of Patent: Jan. 11, 2000

[54] DEVICE FOR OPTICAL ANALYSIS OF SPECIMENS

[75] Inventors: Christer Fåhraeus; Patrik Söderlund, both of Lund; Lennart Sjöstedt, Åryd; Ragnar Segersten, Ängelholm, all of Sweden

[73] Assignee: CellaVision AB, Lund, Sweden

[21] Appl. No.: 08/840,168

[22] Filed: Apr. 14, 1997

[30] Foreign Application Priority Data

Apr. 15, 1996 [SE] Sweden ................................ 9601404

[51] Int. Cl.$^7$ .................................................. G01N 21/01
[52] U.S. Cl. ........................................................ 356/244
[58] Field of Search ............................. 356/244; 118/52, 118/53, 501; 427/2.11, 10, 8, 9, 240

[56] References Cited

U.S. PATENT DOCUMENTS

| | | | |
|---|---|---|---|
| 3,557,267 | 1/1971 | Angelotti et al. | 264/72 |
| 4,016,828 | 4/1977 | Maher, Jr. et al. | 118/6 |
| 4,108,109 | 8/1978 | Barger et al. | 118/52 |
| 4,159,875 | 7/1979 | Hauser | 356/244 |
| 4,197,329 | 4/1980 | Holyrod et al. | 427/2 |
| 5,225,266 | 7/1993 | Menzel | 428/192 |
| 5,326,398 | 7/1994 | Kelly et al. | 118/52 |
| 5,549,750 | 8/1996 | Kelley et al. | 118/55 |
| 5,679,154 | 10/1997 | Kelley et al. | 118/52 |

FOREIGN PATENT DOCUMENTS 25 21 284  12/1975  Germany .

*Primary Examiner*—Frank G. Font
*Assistant Examiner*—Michael P. Stafira
*Attorney, Agent, or Firm*—Cooper & Dunham LLP

[57] ABSTRACT

A device for optical analysis of a specimen, especially a blood sample, is in the form of a dish, a translucent plate-shaped portion, which has a specimen-receiving surface, essentially constituting the bottom of the dish, and a frame, which engages the plate-shaped portion, forming its wall. To catch surplus liquid from the specimen-receiving surface, especially when receiving, smearing, spinning or coloring the specimen, an absorbing material is arranged in a loop along the circumference of the plate-shaped portion. The design of the device permits safe and easy handling of specimens that are injurious to health.

16 Claims, 1 Drawing Sheet

DEVICE FOR OPTICAL ANALYSIS OF SPECIMENS

FIELD OF THE INVENTION

The present invention relates to a device for optical analysis of a specimen, especially a blood sample, said device comprising a translucent, plate-shaped portion having a specimen-receiving surface and a frame which engages the plate-shaped portion.

BACKGROUND OF THE INVENTION

In health service as well as medical service it is common to take specimens of body fluids or tissue and then analyze the specimens under a microscope or by applying some other optical method. To render the analysis possible, the specimens taken must usually be placed on or in some testing device, such as on a glass slide or in a cuvette.

One example of that stated above is so-called differential calculus of white corpuscles, in which the relative distribution of white corpuscles between five main classes of white corpuscles is determined so as to obtain an indication of various states of ill-health.

Traditionally, differential calculus is carried out completely manually. A blood sample is taken from a patient whose blood is to be analyzed. A few drops of the sample are dripped onto a glass slide and are smeared as a thin layer over the surface of the slide by means of an inclined smaller glass slide. Subsequently, the blood is fixed and colored on the slide. Finally, the slide is placed in a microscope, and the blood is studied by a laboratory technician who counts the white blood corpuscles in a suitable area on the slide and determines to which main class each of these belongs.

The manual differential calculus is time-consuming and not very rational. Attempts have therefore been made to automate it in various ways.

For instance, it is known to smear the blood on the slide by means of a spinner. The empty slide is placed manually in a holder in the spinner, whereupon a few drops of blood are dripped onto the slide which is spun, thereby distributing the blood as a thin layer over the slide surface. Then the slide is removed manually from the spinner.

A difficulty in connection with the spinning operation is how the surplus blood, i.e. the blood which during spinning is moved away from the surface of the slide, should be taken care of. Part of the blood is aerosolized at the sharp edge of the slide and settles in various positions inside the spinner, while part of the blood flows over the edge of the slide and gets stuck in the slide holder. Since the handling of blood means a health hazard, all manual handling of surplus blood should be avoided. More or less complicated and, thus, expensive devices having water curtains and exhaust means have been suggested, see e.g. U.S. Pat. No. 4,106,828, to handle surplus blood in the spinner.

U.S. Pat. No. 5,326,398 discloses the arrangement of the slide in a separate plastic case during the spinning operation. The case has small apertures through which blood can be dripped onto the slide, and the case encloses the major part of the slide such that blood that is moved away from the slide is caught in the case. Before and after spinning, the slide is, however, handled manually and without the case.

U.S. Pat. No. 4,197,329 discloses a blood spinner, in which a slide is placed in a recess in a rotatable part. A waste-receiving material in the form of e.g. a sponge is placed around the recess in the rotatable part. During spinning, waste blood is received in the waste-receiving material. Before and after spinning, however, the slide is handled manually in a traditional way. U.S. Pat. No. 4,108,109 discloses a similar spinner.

It is becoming more and more common to carry out differential calculus by means of a flow cell apparatus which automatically analyses the blood in liquid state. In contrast to the above-mentioned methods, the sample is, however, consumed after the analysis in the flow cell apparatus. This means that it is not possible to make a manual second check under microscope if the samples need further checking, which together with the high price of the flow cell apparatus is a considerable drawback of this method. Thus, there is a need of methods for differential calculus that are based on the use of slides which permit both manual and automatic analysis of the sample.

The above optical methods for differential calculus are all based on the use of slides with a varying degree of manual handling. As is well known, a slide is a rectangular plate of glass or plastic, which has two plane-parallel major faces, a sample which is to be analyzed being placed on one major face. However, slides are difficult to handle. They are difficult to pick up, hold and store. They are relatively fragile and may cause wounds in the form of cuts. If the samples that are to be placed on the slides consist of blood or the like which may transmit an infection, the handling thereof involves a health hazard as well.

U.S. Pat. No. 5,225,266 discloses a device, which comprises a rectangular slide surrounded by a rectangular plastic frame. At one short side of the slide, the width of the frame is greater, thereby forming a grip portion. The thickness of the frame is approximately the same as that of the slide.

Moreover, U.S. Pat. No. 4,159,875 discloses a device comprising a rectangular, substantially flat slide holder, one side of which is arranged to support a slide. The holder is designed to protect the slide from being scratched during transport and to permit stacking of slides and alignment of slides in automatic handling.

None of these two prior-art testing devices, however, solves the problem of taking care of surplus testing and/or additive material. Thus, none of them can be used to handle blood or the like in a safe manner.

In view of the above, an object of the invention is to provide a device of the type described by way of introduction, by means of which blood and other specimens can be handled in a safer manner than in the prior-art devices.

This object is achieved by a device according to claim 1. Preferred embodiments are stated in the subclaims.

The new device is in the form of a dish, of which the plate-shaped portion essentially constitutes the bottom. A string of an absorbing material is arranged in a loop along the circumference of the plate-shaped portion. The absorbing material serves to absorb surplus specimen liquid and additive liquid from the specimen-receiving surface of the plate-shaped portion, which reduces the risk that the user comes into contact with the actual specimen. The string of absorbing material is preferably, but not necessarily, arranged in direct contact with the circumference of the plate-shaped portion. The absorbing material further serves a particularly important purpose when the device is used for blood that is spun. By the absorbing material being arranged along the circumference of the plate-shaped portion, the sharp edge at which the blood is normally aerosolized during spinning is in fact eliminated.

Since the absorbing material is part of the device, it is besides obvious that the device has been used, and therefore it cannot be reused by mistake.

The device thus is dish-shaped, which means that it is easy to grasp and that the risk that specimen substance escapes the device is very small, which is advantageous when, for instance, blood is to be transferred directly from the pad of the finger to the specimen-receiving surface.

The frame protects the user from direct contact with the absorbing material. In one embodiment, the string of the absorbing material essentially forms the frame of the device, the outside of the frame being fitted with a protective barrier which prevents absorbed liquid from escaping through the frame.

The frame engages the plate-shaped portion such that the device forms a coherent unit. In one embodiment, the frame and the plate-shaped portion are made in one piece.

The plate-shaped portion is translucent such that optical analysis can be carried out by means of light that is transmitted through the specimen on the specimen-receiving surface. Within the scope of this, the plate-shaped portion could be provided with a reflective layer on the underside such that light can be reflected back through the specimen in the optical analysis.

The inventive device can be used for all types of specimens that are to be smeared on a surface and analyzed optically, but it is particularly advantageous for blood samples.

BRIEF DESCRIPTION OF THE DRAWINGS

The invention will now be described with reference to the accompanying drawings, in which.

DESCRIPTION OF THE PREFERRED EMBODIMENT OF THE INVENTION

Figure 1:
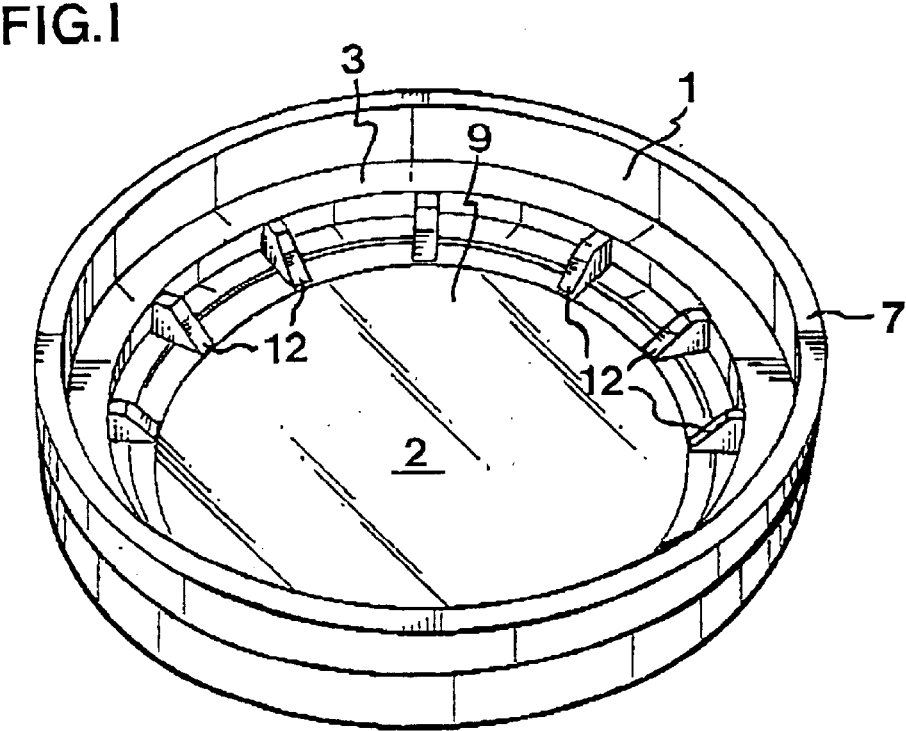
FIG. 1 is a perspective view from above of an embodiment of the invention.
Figure 2:
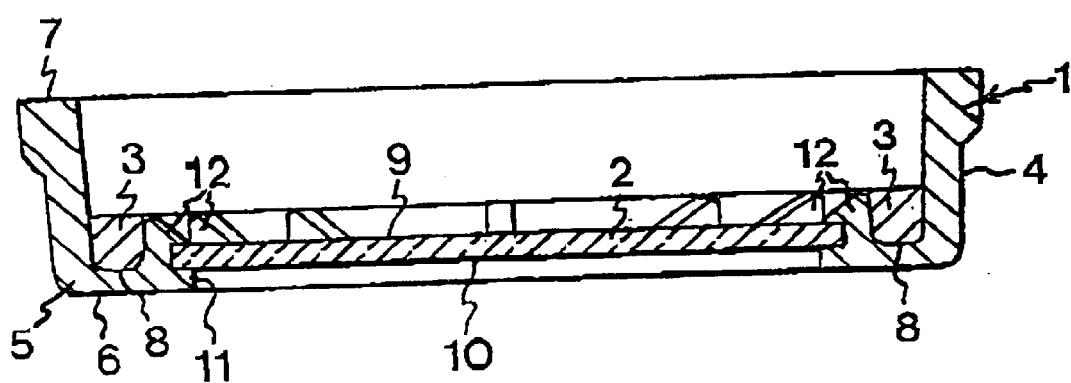
FIG. 2 is a cross-section of the embodiment of the invention illustrated in FIG. 1.

The device shown in FIGS. 1 and 2 essentially consists of a frame 1 of liquid-impermeable material, a translucent plate-shaped portion 2 for receiving a specimen, and a string of absorbing material 3 which forms a loop along the circumference of the plate-shaped portion. The device is in the form of a dish, of which the bottom essentially consists of the plate-shaped portion and the frame essentially forms the wall of the dish. The device is intended for liquid specimens or solid specimens with liquid additives, surplus liquid being absorbed by the absorbing material.

More specifically, the frame 1 constitutes a circular holder for the plate-shaped portion 2 and engages the circumference thereof. The frame has a cylindrical wall portion 4 constituting the wall of the dish, and a bottom portion 5, whose underside forms an annular supporting surface 6 of the device, i.e. a lower edge of the device.

The wall portion 4 has an upper edge 7. In the embodiment illustrated, the outer diameter of the device is slightly greater in the vicinity of the upper edge 7 than in the vicinity of the bottom portion 5, thereby making it possible to stack several devices in each other. The height of the wall portion 4 is essentially greater than the thickness of the plate-shaped portion, but smaller than the radius thereof, a tray being defined by the wall portion 4 and the plate-shaped portion 2. The wall portion 4 serves as a protective barrier for liquid that the absorbing material may not absorb, and as a portion which is easy to grasp and allows safe and simple handling of the device.

In the bottom of the dish, more specifically in the upper side of the bottom portion 5 and adjacent to the inside of the wall portion, there is formed an annular groove 8 for receiving the absorbing material 3.

In the embodiment illustrated, the plate-shaped portion is a circular glass plate having two plane-parallel major faces 9, 10. The plate-shaped portion engages along its circumference with the frame 1 in a stepped portion 11 in the bottom portion 5 and is held by means of fixing lugs 12 projecting from the bottom portion at regular intervals. The plate-shaped portion thus is arranged closer to the annular supporting surface 6 of the bottom portion than the upper edge 7 of the wall portion, but yet at a certain distance from the supporting surface 6, such that the device can be placed on a surface, without any risk that the underside 10 of the plate-shaped portion is scratched. If desired, the plate-shaped portion can be made to be releasable from the frame. This can be accomplished, for instance, by making the fixing lugs elastic, in which case the string of absorbing material serves as a locking ring for the fixing lugs. Of course, other fixing means than fixing lugs can be used to hold the plate-shaped portion. Alternatively, the plate-shaped portion can be made in one piece with the frame. The entire device may be, for example, injection-molded in plastic.

The upper major face 9 of the plate-shaped portion constitutes a specimen-receiving surface. The surface may, if desirable, be prepared in some suitable manner in connection with manufacture, for instance with a reagent, a colorant, antibodies or agar for growing bacteria.

Preferably, the absorbing material consists of a porous material such that surplus liquid can be absorbed by capillary attraction, or of a material of a fine structure that may absorb surplus liquid examples of suitable materials are polymer or fiber matrices, e.g. sintered plastic, cellulose, paper or cotton wool. A bactericide, such as Gevesol or a wood-impregnating agent, is suitably added. As mentioned above, the absorbing material results in the device being disposable.

The base of the groove 8 and, thus, the lower edge of the absorbing material are, in the embodiment shown, positioned closer to the lower edge 6 of the device than the specimen-receiving surface of the plate-shaped portion, such that liquid tends to move into and downwards in the absorbing material. The absorbing material further is of such a thickness that the specimen-receiving surface is positioned below the upper edge of the absorbing material. As a result, there is no sharp edge at the circumference of the plate-shaped portion, which may cause aerosolizing. Instead of arranging the absorbing material in the groove 8, it would be possible to arrange it on the specimen-receiving surface at the circumference thereof. However, then the advantage would not be obtained that liquid moves downwards into the absorbing material.

The device can be provided with a detachable cover or a seal (not shown) which protects the specimen-receiving surface and keeps it free from dust. When the device is to be used for blood samples, it may be provided with, for instance, a thin perforatable plastic film. The blood sample can then be injected through the plastic film, which is retained during spinning and coloring so as to further decrease the risk that blood escapes the device. Later on, when the blood sample is to be analyzed, the plastic film is pulled off.

The outside of the device is cylindrical, which makes it easy to grip and place in a holder in various apparatus, since its angular position does not matter. Moreover, the specimen-receiving surface is circular, which is advantageous since it yields the greatest possible surface of analysis in relation to the circumference of the surface of analysis. It is advantageous from the viewpoint of manufacture, especially If the entire device is injection-molded in plastic, that it is rotationally symmetrical about an axis extending perpendicular to the specimen-receiving surface because a symmetric distribution of force will then be obtained. However, it is not necessary to have rotational symmetry, but the shape of a dish and the absorbing material confer great advantages compared with prior-art slides, also when the device Is of a cross-section other than circular.

In an alternative embodiment, the frame may consist of an absorbing material, in which case the string of absorbing material may constitute an integrated part of the frame. With a view to preventing liquid from escaping through the frame in this embodiment, the outside of the frame is provided with a liquid-impermeable protective barrier. This can be accomplished, for instance, by lacquering the absorbing material.

As mentioned above, the described device can advantageously be used for safe handling of blood samples, especially those intended to be spun and analyzed optically, such as In differential calculus. However, the device is also advantageous for other samples, such as cervical smears and culture of bacteria, that are to be analyzed optically.

What we claim and desire to secure by Letters Patent is:

1. A device for optical analysis of a specimen, comprising a translucent, plate-shaped portion having a specimen-receiving surface and a frame which affixes to the plate-shaped portion, wherein the device is in the form of a dish, the plate-shaped portion essentially constituting the bottom of the dish; and wherein a string of absorbing material, which is adapted to absorb liquid from the specimen-receiving surface, is arranged in a loop along the circumference of the plate-shaped portion.

2. The device as claimed in claim 1, wherein the string of absorbing material is received in a groove formed in the frame.

3. The device as claimed in claim 2, wherein the specimen-receiving surface is positioned closer to the lower edge of the frame than the upper edge thereof, and wherein the base of the groove of the frame is positioned between the lower edge of the frame and the specimen-receiving surface.

4. The device as claimed in claim 1, wherein the frame has at least the same height as the absorbing material.

5. The device as claimed in claim 1, wherein the frame consists of absorbing material, and wherein the frame is provided with a liquid-impermeable protective barrier on its outside.

6. The device as claimed in claim 1, the device being essentially rotationally symmetrical about an axis extending perpendicular to the plate-shaped portion.

7. The device as claimed in claim 1, wherein the frame has an essentially cylindrical outside.

8. The device as claimed in claim 1, wherein the specimen-receiving surface has a substantially circular circumference.

9. The device as claimed in claim 1, wherein the absorbing material consists of a polymer or fiber matrix.

10. The device as claimed in claim 1, wherein the absorbing material contains a bactericide.

11. The device as claimed In claim 1, the device being fitted with a perforatable cover.

12. The device as claimed in claim 1, wherein the frame and the plate-shaped portion are made in one piece.

13. A device for optical analysis of a specimen; comprising a dish, the dish comprising:

a frame having a perimeter wall with an inner portion, an outer portion, and a bottom edge;

a translucent plate for receiving the specimen which affixes to the frame proximate the bottom edge of the wall to form a bottom of the dish; and a string of liquid absorbing material arranged along the inner portion of the wall for absorbing liquid from the specimen;

such that the outer portion of the wall provides means for handling the dish without contacting the specimen.

14. A method of optical analysis of a specimen, comprising the steps of:

placing the specimen on a translucent plate which is mounted proximate a bottom edge of a wall of a frame and affixes to the wall along a perimeter of the plate to form a bottom of a dish, a string of a liquid absorbing material arranged along an inner portion of the wall;

placing the dish by handling the frame in position for an apparatus to operate on the specimen;

operating the apparatus; and removing the dish from the apparatus by handling the frame.

15. The method of claim 14, wherein the apparatus comprises a spinner.

16. The method of claim 14, wherein the apparatus comprises an optical analysis device.

* * * * *